United States Patent [19]

Cowles et al.

[11] Patent Number: 4,529,707

[45] Date of Patent: Jul. 16, 1985

[54] DETECTION OF BORON IMPURITIES IN CHLOROSILANES

[75] Inventors: Harold R. Cowles, Troy; William D. Kray, Burnt Hills, both of N.Y.

[73] Assignee: General Electric Company, Waterford, N.Y.

[21] Appl. No.: 420,650

[22] Filed: Sep. 21, 1982

[51] Int. Cl.³ .......................... G01N 1/28; G01N 21/78
[52] U.S. Cl. ..................................... 436/72; 423/264; 423/292; 423/341; 436/124; 436/164; 436/178; 436/182
[58] Field of Search ................. 436/164, 182, 72, 124, 436/174, 177, 175, 178; 423/264, 292, 341, 343

[56] References Cited

U.S. PATENT DOCUMENTS 3,126,248  3/1964  Pohl et al. .
3,403,003  9/1968  Morgenthaler .
4,042,331  8/1977  Schmidt et al. .
4,409,195  10/1983  Darnell et al. ...................... 423/341

OTHER PUBLICATIONS

Marczenko, Chemia Analityczna, vol. 14, pp. 1331-1338, 1969.
McCusker et al, "Reactions of Haloboranes with Organosiloxanes", 1957.
Churbanov et al, "Chemical Abstracts", vol. 64, #20175a, 1966.
Vecsenyes, "Chemical Abstracts", vol. 65, #19296h, 1966.
Haas et al, "Anal. Chem.", vol. 36:1, pp. 245-246, 1964.

*Primary Examiner*—Barry S. Richman
*Assistant Examiner*—Robert J. Hill, Jr.

[57] ABSTRACT

A method for preparing a chlorosilane sample to enable colorimetric detection of the presence of minute amounts of boron impurities is provided. Detection of boron impurities below five parts per billion is contemplated.

8 Claims, No Drawings

DETECTION OF BORON IMPURITIES IN CHLOROSILANES

This invention relates to a method for the detection of boron impurities in chlorosilanes. More particularly, it relates to a method of preconcentrating boron compounds in a chlorosilane sample in order to lower the accurate detection limit for spectrophotometric determination of boron content below about 5 parts per billion (ppb).

Silicon of extremely high purity is required for sophisticated electronics uses such as in transistors and semiconductors. It is well known that even trace impurities can seriously impair the performance of silicon-containing electronic components.

Metallic silicon for semiconductor use is conventionally prepared by reduction of silicon halides, such as silicon tetrachloride ($SiCl_4$), trichlorosilane ($HSiCl_3$) and dichlorosilane ($H_2SiCl_2$), with hydrogen, zinc, sodium, or metal hydrides. Silicon may also be derived from thermal decomposition of silane ($SiH_4$), but this latter material is hard to work with because it burns explosively on contact with air.

One of the most difficult impurities to remove from hyperpure silicon is boron. Whereas other common impurities such as copper, iron and manganese are comparatively easy to remove by conventional distillation or recrystillization techniques (e.g., zone refining, crystal pulling), boron has physical properties so similar to silicon that separation is accomplished only by repeated trials. Moreover, concentrating purification efforts on the starting materials, e.g., chlorosilanes, is likewise difficult because boron forms corresponding compounds with similar properties.

Boron removal technology, however, has developed and improved steadily. Most recently, as disclosed in commonly-assigned copending U.S. patent application Ser. No. 359,437, filed Mar. 18, 1982 (hereby incorporated by reference), the ability to almost totally remove boron halides from chlorosilanes has been developed. In that technology, silicon halide solutions are treated with organosiloxanes. The siloxanes react or complex with the impurities to form thermally stable compounds which are left behind in a distillation of the chlorosilane.

Along with a need to remove boron impurities from silicon there arises the need to detect the presence of boron; and as removal technology improves, the ability to detect boron must correspondingly become sensitive to lesser and lesser amounts of boron.

Currently the most accurate methods for determining levels of boron in chlorosilanes are a modified "curcumin method", described by Z. Marczenko, *Chemia Analityczna*, Vol. 14, pp. 1331–1338 (1969), and colorimetric determination after extractive separation of boron, described by C. Haas, R. Pellin and M. Everingham, *Anal. Chem.*, Vol. 36:1, pp. 245–6 (Jan. 1964). Both articles are incorporated herein by reference. In the former method, a chlorosilane sample is treated with mannitol to form a non-volatile compound with boron, the chlorosilane is hydrolyzed and fluorinated, then drawn off, leaving the boron compound residue, to which curcumin is added. Curcumin [1,7-bis-(4-hydroxy-3-methoxyphenyl)-1,6-heptadiene-3,5-dione], in an acid, non-aqueous medium, reacts with cationic boron to form rosocyanin, a red colored complex. Protonated curcumin not bound to boron is yellow in coloration, so that the absorption of samples at a reference wavelength (e.g., 540 nm) gives a quantitive indication of the presence of boron.

In the latter method, boron is extracted from a chlorosilane sample with a quinalizarin-sulfuric acid reagent. Quinalizerin [1,2,5,8-tetrahydroxyanthaquinone] dissolved in concentrated sulfuric acid gives an intense blue-violet solution; and addition of water shifts the color to red. If the water or acid solution contains borate, the red shift is less, with a high enough boron content causing a reversal to blue-violet. This color change is the basis for spectrophotometric analysis at 620 nm.

The drawback of these methods is that they are designed to detect boron in chlorosilanes at levels an order of magnitude greater than the reduced levels now obtainable. Consequently a need for accurate detection of boron present in less than 5 parts per billion (ppb) in chlorosilanes is needed.

A method has now been discovered for preconcentrating all the boron present in a large sample of chlorosilane and extracting it from the chlorosilane so that the total boron may be analyzed, without interference from the reactive chlorosilane. The method involves treating the sample with chlorine to convert any present boranes to boron halides, introducing siloxane to complex with the boron, and removing the chlorosilane to leave a residue, containing substantially all the boron of the original sample, to be analyzed.

Accordingly, it is the object of the present invention to provide a simple procedure for accurately determining the boron content of chlorosilanes.

It is a further object of the present invention to make possible the detection of boron impurities in chlorosilanes at levels of 5 ppb or less.

It is a further object of the present invention to provide a means of preparing chlorosilane samples for boron assay which will avoid analytical interference from the chlorosilane.

These and other objects are accomplished herein by a method for preparing a chlorosilane sample for quantitative analysis of boron impurities comprising:

(1) treating the chlorosilane sample with chlorine;
(2) introducing a stoichiometrically large amount of a siloxane to the sample; and
(3) removing the chlorosilane in an inert, anhydrous atmosphere.

An additional feature contemplated in the present invention is a method for analyzing the quantity of boron impurities in a sample of chlorosilane comprising:

(1) treating the chlorosilane sample with chlorine;
(2) introducing a stoichiometrically large amount of a siloxane to the sample;
(3) removing the chlorosilane in an inert, anhydrous atmosphere;
(4) adding to the residue a reagent which forms a colored complex with boron; and
(5) spectrophotometrically determining the boron content of said complex.

DETAILED DESCRIPTION OF THE INVENTION

The method of this invention involves contacting the boron halide impurity present in a chlorosilane solution with a molar excess of an organosiloxane, bringing about a reaction between the impurity and the siloxane to yield compounds of greater stability than the chlorosilane, and then removing the chlorosilane, leaving the siloxane-bound impurities behind to be analyzed. This method is very effective for assaying boron contaminates, especially from solutions of trichlorosilane. The boron concentration in a solution of trichlorosilane can be accurately measured by the method of the present invention at levels of 0–5 parts per billion.

The siloxane compounds suitable for the purposes herein are any organosiloxanes which will react with the boron impurity present in the chlorosilane solution to form impurity-siloxane compounds (e.g., borosiloxane) allowing removal of the silane and further analysis of the complexed boron. These siloxanes include alkyl, aryl, halogenated alkyl, halogenated aryl or hydrogen substituted alkyl or aryl cyclotrisiloxanes and cyclotetrasiloxanes such as hexamethylcyclotrisiloxane, octamethylcyclotetrasiloxane, polydimethylsiloxane fluids, dimethylmethyl hydrogen siloxane copolymers and other cyclic siloxane monomers. Cyclotrisiloxanes, alkyl cyclotrisiloxanes, halogenated alkyl cyclotrisiloxanes are preferred; hexamethyl cyclotrisiloxane is most preferred.

The siloxanes are added to the chlorosilane sample to be analyzed in an amount which will ensure reaction of the siloxanes with the boron impurities. Best results are obtained if this amount is a large molar excess to ensure that *all* of the impurity present in the sample is effectively bound by the siloxane. The amount of siloxane required of course will vary based on the purity of the sample, but for relatively pure samples (boron content <5 ppb), 1 part siloxane per 100 of chlorosilane in the sample has produced good experimental results. However, any amount which effectively binds substantially all of the boron impurity present is contemplated. Also to ensure complete binding of all the boron present, the sample is first treated with chlorine to convert any boranes present, such as $B_2H_6$, to the less volatile halide form, $BCl_3$.

After the siloxane is mixed with the sample, the chlorosilane can be drawn off so as not to affect subsequent analysis of the siloxane-complexed boron. This is best accomplished by evaporation in an inert, anhydrous environment, such as under dry, purified nitrogen. Because chlorosilanes such as trichlorosilane and silicon tetrachloride are fuming liquids at room temperature and decompose on contact with water, the dry, inert purge prevents side reactions which could affect the analytical results.

The siloxane residue remaining after elimination of the chlorosilane contains substantially all the boron which was originally present in the sample. The residue may be developed at this point for quantitative spectrophotometric analysis.

For the purposes of this invention, "spectrophotometric analysis" refers to any means of detecting the presence or quantity in a sample of a particular chemical system by observing the chemical system's characteristic absorptivity for radiant energy, including visible light, infra-red radiation, ultraviolet radiation, etc. "Colorimetric analysis" refers to spectrophotometric analyses which involve the observation of a system's absorption for radiation in the visible spectrum (400–750 nm). Samples prepared according to the present invention are suitably analyzed by a variety of spectrophotometric techniques, including but not limited to Fourier transformation infra-red analysis, spark source mass spectrophotometry, and colorimetric spectrophotometry.

In the latter method, which is preferred herein, the siloxane residue may be developed with a colorimetric reagent and the boron then quantitatively assayed by spectrophotometer. Any reagent which forms a colored complex with boron suitable for spectrophotometric analysis, and is not inhibited by the presence of the siloxane, may be employed in the present invention. Good results have been observed using the quinalizarin-concentrated sulfuric acid reagent in the aforementioned Haas et al. article. It is prepared by dissolving 1 part by weight quinalizarin in 368 parts concentrated sulfuric acid (sp. gr. 1.84). This reagent is stable for approximately 3 days, and unnecessary exposure to light and air should be avoided.

In preparing a siloxane residue for boron assay, the entire residue is dissolved in a measured quantity of the quinalizarin-sulfuric acid reagent. In the presence of boron, the colored complex will develop and spectrophotometric analysis at 630 nm, using water as a reference, will indicate boron level when compared against a calibration plot. The calibration curve, prepared by analyzing reference solutions of $BCl_3$ added gravimetrically to hyperpure chlorosilane, has been found to be linear from about 0 up to 5 parts per billion by weight, making the analytical method of this invention especially accurate for extremely pure samples of chlorosilane.

In order that those skilled in the art may better understand how to practice the present invention, the following examples are offered by way of illustration and not by way of limitation.

EXAMPLE 1

General Procedure

To generate a calibration curve, reference solutions of boron trichloride in hyperpure trichlorosilane (TCS) are prepared at concentrations of 0.1 ppbw to 3.0 ppbw in increments of 0.2 ppbw. 100.0 grams TCS reference samples are each added to a reaction vessel and 1.0 gram of hexamethylcyclotrisiloxane mixed in. Dry purified nitrogen is passed over the solution surface to slowly purge the vessel of TCS, leaving a solid siloxane residue. 10.0 ml. of freshly prepared quinalizarin-sulfuric acid reagent (1 pbw quinalizarin per 368 pbw concentrated sulfuric acid) are added to the vessel, generating a colored solution which is spectrophotometrically analyzed at 630 nm in a 1 cm cell referenced with water. The absorbance of each reference solution at 630 nm is plotted to produce a calibration curve.

A sample of TCS is analyzed for the presence of boron by adding 100.0 grams of the TCS to a vessel, bubbling chlorine gas through the sample for approximately 2 min., adding 1.0 gram hexamethylcyclotrisiloxane to the solution, and purging the volatile TCS slowly with dry purified nitrogen. The residue is dissolved in 10.0 ml. of the quinalizarin-sulfuric acid reagent, and the resulting colored solution analyzed as above at 630 nm. Comparison of the absorbance observed for the sample with the calibration plot is an indication of the level of boron present in the sample.

Obviously, modifications and variations in the present invention are possible in light of the foregoing disclosure. It is understood, however, that any incidental changes made in the particular embodiments of the invention as disclosed are within the full intended scope of the invention as defined by the appended claims.

We claim:

1. A method for quantitative spectrophotometric analysis of boron impurities in a sample of chlorosilane comprising:
    (1) treating the chlorosilane sample with sufficient chlorine to ensure full chlorination of the boron impurities;
    (2) introducing a stoichiometrically large amount of a siloxane selected from the group consisting of cyclotrisiloxane, cyclotetrasiloxane, alkyl, aryl, halogenated alkyl and halogenated aryl substituted cyclotrisiloxanes and cyclotetrasiloxanes, polydimethylsiloxane fluids, and dimethyl-methylhydrogensiloxane copolymers to the sample to ensure reaction with substantially all the boron impurities to form borosiloxane compounds;
    (3) removing the chlorosilane in an inert, anhydrous atmosphere leaving a solid residue comprising siloxane and the borosiloxane compounds;
    (4) developing the solid residue for spectrophotometric analysis by adding a reagent which forms a colored complex with boron suitable for spectrophotometric analysis and is not inhibited by the presence of said siloxane; and
    (5) spectrophotometrically determining the boron content of said residue.

2. A method as defined in claim 1, wherein said chlorosilane is trichlorosilane.

3. A method as defined in claim 2, wherein said siloxane is a cyclotrisiloxane.

4. A method as defined in claim 3, wherein said cyclotrisiloxane is hexamethylcyclotrisiloxane.

5. A method as defined in claim 1, wherein said removal step (3) is an evaporation by dry nitrogen purge.

6. A method as defined in claim 1, wherein the spectrophotometric determination of step (5) is a colorimetric determination.

7. A method as defined in claim 6, wherein said reagent comprises quinalizarin and concentrated sulfuric acid.

8. A method as defined in claim 7, wherein said reagent comprises 1 part by weight quinalizarin dissolved in approximately 368 parts by weight sulfuric acid.

* * * * *